United States Patent [19]
Kishida

[11] Patent Number: 5,630,179
[45] Date of Patent: May 13, 1997

[54] OPHTHALMOLOGICAL IMAGING APPARATUS

[75] Inventor: Nobuyoshi Kishida, Yokohama, Japan

[73] Assignee: Canon Kabushiki Kaisha, Tokyo, Japan

[21] Appl. No.: 325,823

[22] Filed: Oct. 19, 1994

[30] Foreign Application Priority Data

Oct. 22, 1993 [JP] Japan .................................. 5-287561
Sep. 12, 1994 [JP] Japan .................................. 6-243269

[51] Int. Cl.$^6$ .............................. G03B 29/00; G03B 9/08
[52] U.S. Cl. ........................................ 396/18; 351/206
[58] Field of Search ............................ 351/221, 206,
351/207, 233, 243, 216; 354/62, 132, 75,
76; 396/18

[56] References Cited

U.S. PATENT DOCUMENTS

| | | | |
|---|---|---|---|
| 2,408,764 | 10/1946 | Edgerton | 354/132 |
| 4,414,608 | 11/1983 | Furihata . | |
| 4,887,106 | 12/1989 | Cooper, Jr. | 354/62 |
| 5,141,303 | 8/1992 | Yammamoto et al. | 351/221 |
| 5,279,298 | 1/1994 | Flower | 351/221 |
| 5,300,964 | 4/1994 | Kobayashi | 351/207 |
| 5,341,180 | 8/1994 | Isogai et al. | 351/206 |
| 5,347,994 | 9/1994 | Takahashi et al. | 354/62 |
| 5,355,186 | 10/1994 | Akiyama | 351/221 |
| 5,394,199 | 2/1995 | Flower | 351/221 |

*Primary Examiner*—Safet Metjahic
*Assistant Examiner*—Nicholas J. Tuccillo
*Attorney, Agent, or Firm*—Fitzpatrick, Cella, Harper & Scinto

[57] ABSTRACT

An ophthalmological imaging apparatus includes a main body portion, an internal power source and an external power source. The main body portion has a light source producing light for imaging the eye to be examined. The internal power source is provided in the main body portion and supplies electrical energy to the light source for the production of the light. The external power source is provided discretely from the main body portion and supplies from outside of the main body portion electrical energy to the light source corresponding to the deficiency in the amount of light from the light source produced by the electrical energy from the internal power source relative to a desired amount of light for imaging.

15 Claims, 10 Drawing Sheets

OPHTHALMOLOGICAL IMAGING APPARATUS

BACKGROUND OF THE INVENTION

1. Field of the Invention

This invention relates to an ophthalmological photographing apparatus for use in ophthalmic hospitals or the like.

2. Related Background Art

Heretofore, an ophthalmological photographing apparatus such as a retinal camera has generally been designed such that it can effect color photographing of the fundus of an eye and fluorescence photographing of the fundus of the eye. In the fluorescence photographing of the fundus of the eye, a contrast medium flowing through the blood vessels of the fundus of an eye to be examined into which the contrast medium has been intravenously injected is excited by exciting light for illumination and fluorescence created at this time is directed to film or an image pickup element to thereby effect the photographing of the fundus of the eye.

However, in fluorescence photographing of the fundus of the eye, the amount of light needed for performing such photographing is several times as much as that in the case of color photographing of the fundus of the eye, and further, to observe the initial state of the intravenous injection of the contrast medium or the state of the flow of blood in the blood vessels as a variation with time, it is necessary to effect continuous photographing at a speed of about a sheet per second. Thus, a power source for rapid charging which causes a flash lamp to continuously emit light becomes necessary.

On the other hand, in the case of color photographing of the fundus of the eye, it is not particularly necessary to effect continuous photographing and the photographing interval can be long. Therefore, a power source for rapid charging is unnecessary and further, when the fluorescence photographing of the fundus of the eye is not effected, the power source for rapid charging is likewise unnecessary.

Accordingly, a power source of large capacity contained in an ophthalmological photographing apparatus increases the bulk of the entire apparatus as well as increasing the costs to manufacture it, and this is very disadvantageous in practical use.

SUMMARY OF THE INVENTION

In view of the above-described example of the prior art, the present invention has as a first object thereof the provision of an ophthalmological photographing apparatus using a compact internal power source and only when the amount of light for photographing is deficient, electrical energy is supplied from outside the apparatus so as to be capable of coping with various amounts of light needed for photographing while effectively utilizing the internal power source.

Other objects of the present invention will become apparent from the following detailed description of some embodiments of the invention.

DETAILED DESCRIPTION OF THE PREFERRED EMBODIMENTS

Figure 1:
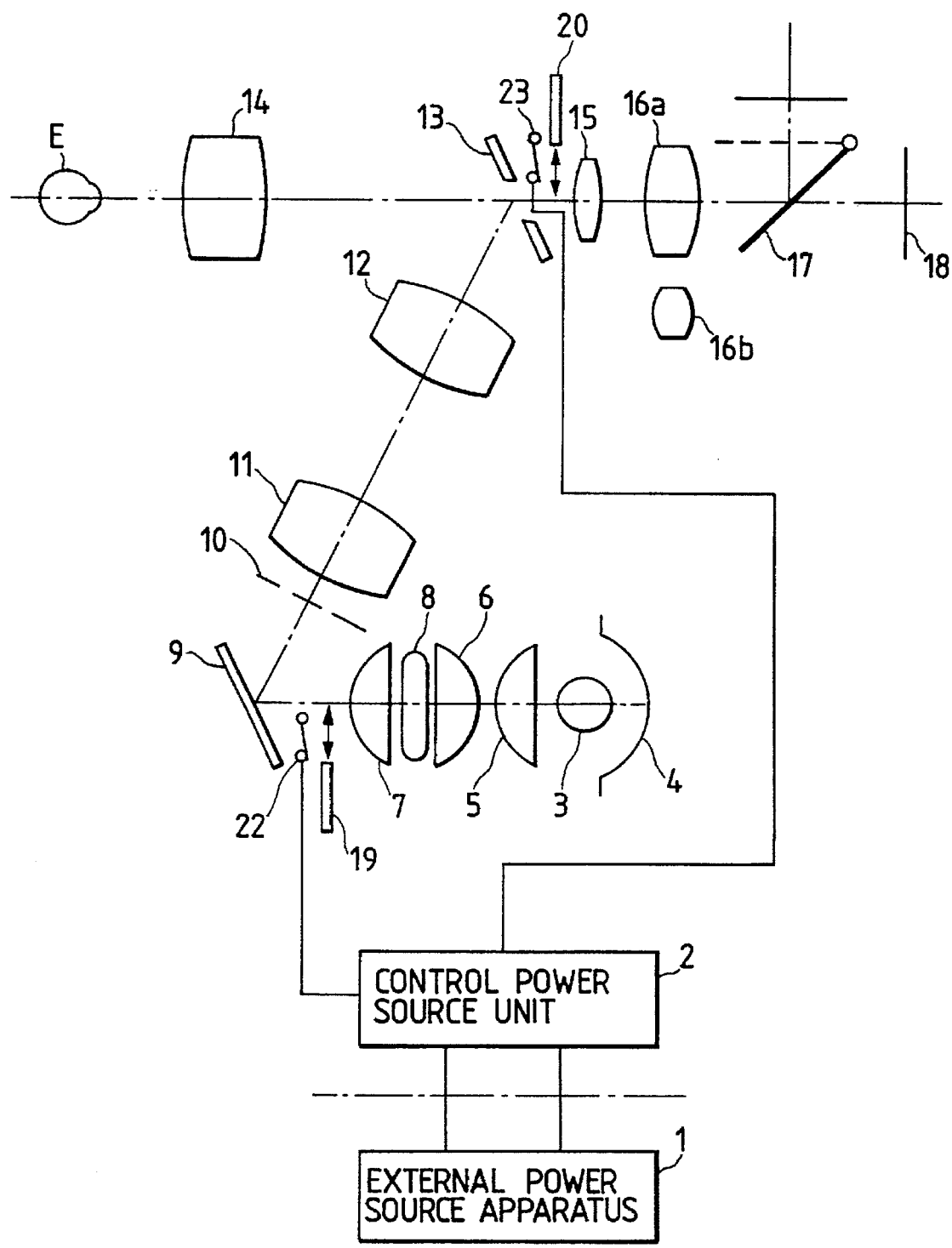
FIG. 1 shows the construction of a first embodiment of the present invention.

The present invention will hereinafter be described in detail with respect to some embodiments thereof shown in the drawings.

FIG. 1 shows a first embodiment in which the present invention is applied to a retinal camera. An external power source apparatus 1 provided externally of a retinal camera body is capable of being connected to the control power source unit 2 of the retinal camera body through a connecting member such as a connector. The illuminating optical system of the retinal camera has optical members such as a light source 3 for observation comprising a halogen lamp, a reflector 4, condenser lenses 5, 6, 7, a light source 8 for photographing comprising a xenon lamp, a reflecting mirror 9, a ring slit 10, relay lenses 11, 12, an apertured mirror 13 and an objective lens 14.

Also, as a photographing optical system, there are provided a focusing lens 15, an imaging lens 16a, a quick return mirror 17 and film 18 rearwardly of the apertured mirror 13. The imaging lens 16a is interchangeable with an imaging lens 16b of different magnification.

Further, a fluorescence exciter filter 19 for fluorescence photographing and a barrier filter 20 are removably disposed in the illuminating optical system and the photographing optical system, respectively, and detection switches 22 and 23 for detecting the insertion of these filters 19 and 20 are provided, and the detection signals S1 and S2 of these detection switches 22 and 23, respectively, are connected to the control power source unit 2.

When observing the fundus of an eye E to be examined, illuminating light from the light source 3 for observation is directed to the fundus of the eye E to be examined via the condenser lenses 5, 6, 7, the reflecting mirror 9, the ring slit 10, the relay lenses 11, 12, the apertured mirror 13 and the objective lens 14. Also, when photographing the fundus of the eye, illuminating light from the light source 8 for photographing is directed to the fundus of the eye E to be examined via the optical members similar to those during the observation.

The reflected light from the fundus of the eye E to be examined is directed to an observation finder or a CCD camera, not shown, by a quick return mirror 17 during the observation, via the objective lens 14, the aperture mirror 13, the focusing lens 15 and the imaging lens 16a which constitute the photographing optical system, and during the photographing, the quick return mirror 17 is retracted from the optical path of the reflected light and the reflected light is directed to 35 mm film 18 for photographing or instant film or a CCD camera or the like.

An examiner can change over the imaging lenses 16a and 16b to thereby change the photographing magnification. The control power source unit 2 for effecting the control of the power source detects the insertion and retraction of the fluorescence exciter filter 19 for fluorescence photographing and the barrier filter 20 effected by the examiner. When in this detected state, the fundus of the eye E to be examined is to be recorded as a static image, and when the examiner depresses a photographing start switch, not shown, the quick return mirror 17 is retracted from the photographing optical system and the light source 8 for photographing emits light.

Figure 2:
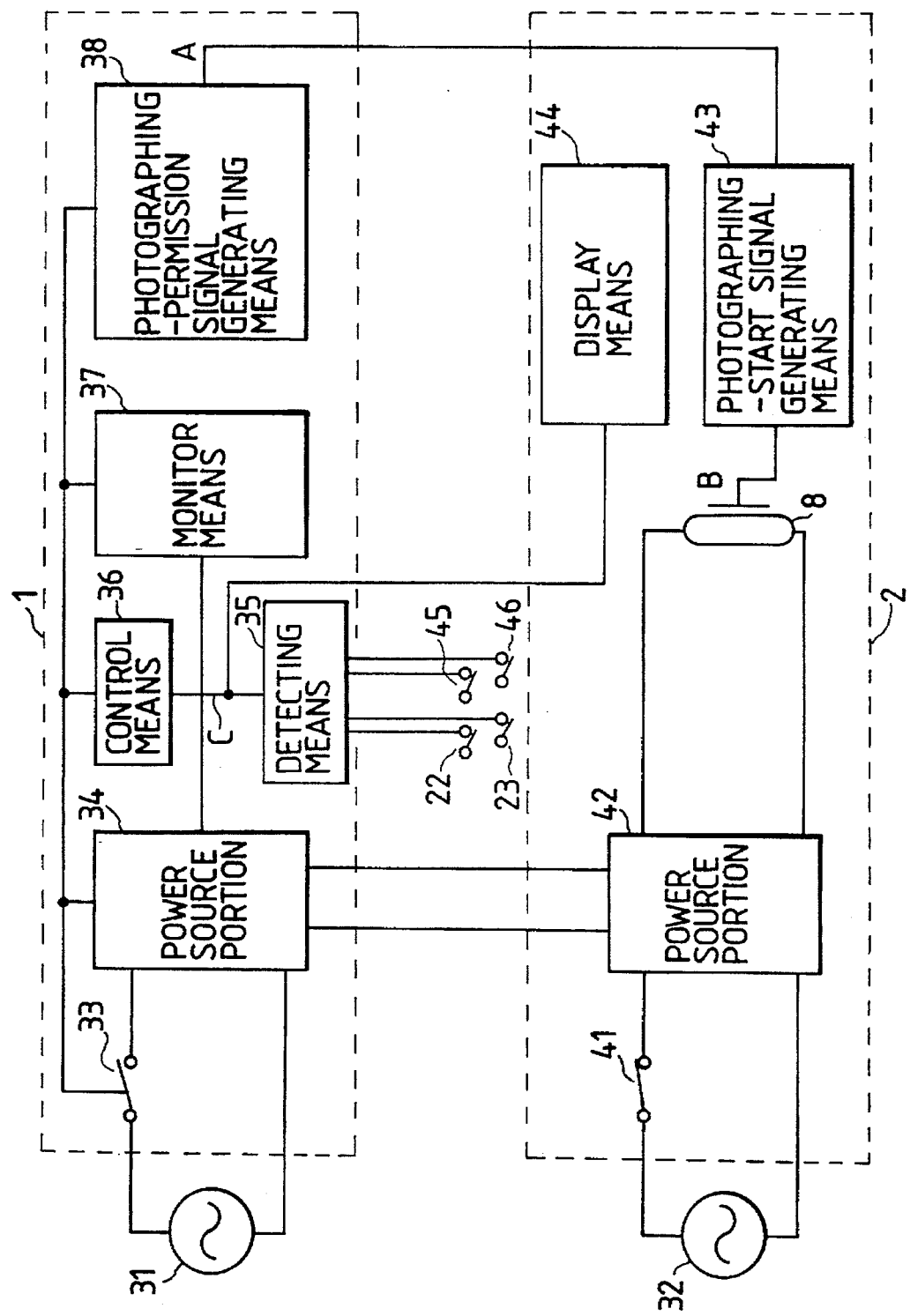
FIG. 2 is a block circuit diagram of a power source portion.

FIG. 2 is a block circuit diagram of a power source portion. A commercially available power source 31 is connected to the external power source apparatus 1, and a commercially available power source 32 is connected to the control power source unit 2. The external power source apparatus 1 is comprised of a power source switch 33, a power source portion 34, detecting means 35 for detecting the deficiency of the amount of light needed for photographing, control means 36 for controlling the power source switch 33 and the power source portion 34 on the basis of the output from the detecting means 35, monitor means 37 for monitoring the voltage of the power source portion 34, and photographing permission signal generating means 38 for generating a photographing permission signal A on the basis of the output from the monitor means 37.

The control power source unit 2 is comprised of a power source switch 41, a power source portion 42 for causing the light source 8 for photographing in FIG. 1 to emit light, photographing-start signal generating means 45 for generating a photographing-start signal B to the light source 8 for photographing, and indicating means 46 for indicating that the external power source apparatus 1 has been actuated. Further, inputs from a detection switch 22 for detecting that the fluorescence exciter filter 19 has been inserted into the illuminating optical system, a switch 23 for detecting that the fluorescence barrier filter 20 has been inserted into the illuminating optical system, a switch 45 for shortening the photographing interval, and a switch 46 for setting the light amount for photographing are outputted to the external power source apparatus 1.

In the control power source unit 2, when the power source switch 41 is closed, the power source portion 42 is actuated and is charged to a predetermined voltage, whereafter energy is supplied to the light source 8 for photographing by the photographing-start signal B, and this energy is converted into light and is used as illuminating light for photographing.

In the external power source apparatus 1, if the detection switch 22 for the fluorescence exciter filter 19 is ON and the detection switch 23 for the fluorescence barrier filter 20 is ON, the detecting means 35 determines that the mode of fluorescence photographing. When it is judged by the switch 45 for shortening the photographing interval and the switch 46 for setting the light amount for photographing that the light amount for continuous photographing is deficient by the pre-inputted supply energy of the power source portion 42 of the control power source unit 2, an external power source actuating signal C is outputted from the detecting means 35. The indicating means 44 of the control power source unit 2 indicates that the external power source apparatus 1 has been actuated by the inputting of the external power source actuating signal C. The external power source actuating signal C includes energy data generated by the power source portion 34 of the external power source apparatus 1 which is equivalent to an amount of energy deficient in the power source portion 42 of the control power source unit 2, and is inputted to the control means 36.

Figure 3:
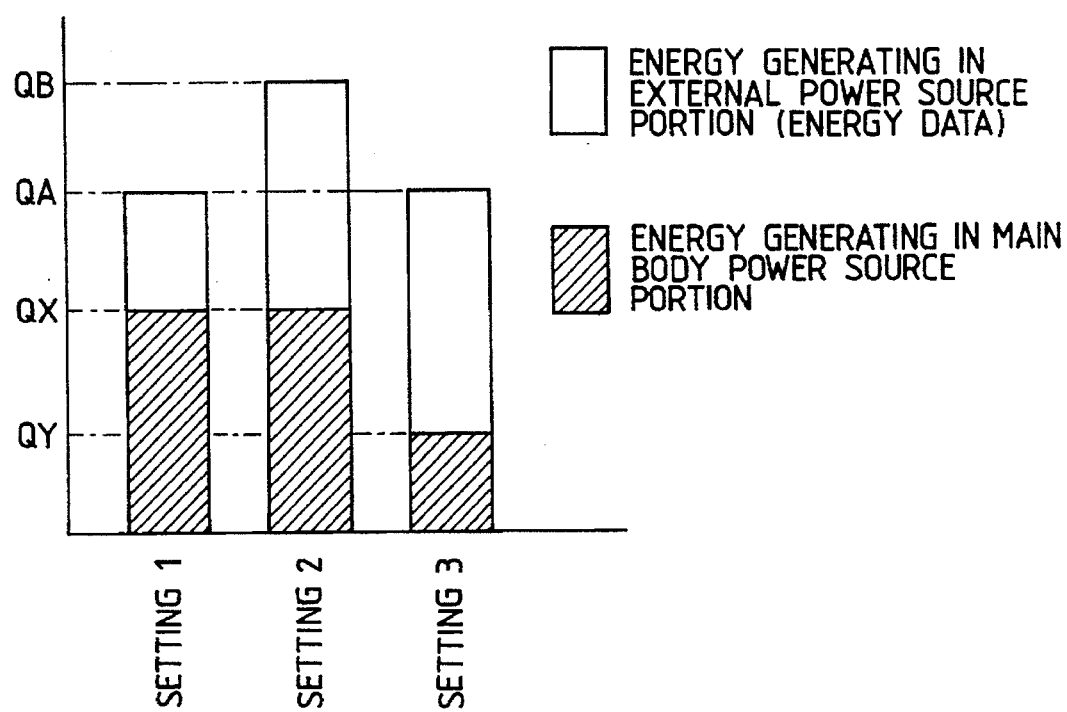
FIG. 3 is a graph showing the light amounts for photographing by a main body power source apparatus and an external power source apparatus.

The energy data supplied from the external power source apparatus 1 to the control power source unit 2 are determined as shown in FIG. 3. That is, in setting 1, a portion corresponding to QA–QX is represented by corresponding energy data. When the light amount for photographing is increased from QA to QB, QB–QX shown in setting 2 is represented by corresponding energy data. When the photographing interval is shortened from setting 1, QA–QY shown in setting 3 is represented by corresponding energy data.

The control means 36 closes the power source switch 33 of the external power source apparatus 1, converts the energy data into charging voltage data and actuates the power source portion 34 of the external power source apparatus 1. After being actuated, the power source portion 34 is charged to a voltage corresponding to the energy data, by the charging voltage data from the control means 36. The charging voltage of the power source portion 34 is inputted to the monitor means 37, and is compared with the charging voltage data from the control means 36, and when charging is completed, the photographing permission signal A is outputted from the photographing permission signal generating means 38. The energy charged to the power source portion 34 joins the energy charged to the power source portion 42 of the control power source unit 2 by the photographing-start signal B because the power source portion 34 is parallel-connected to the power source portion 42 of the control power source unit 2, whereafter it is supplied to the light source 8 for photographing.

By the external power source apparatus 1 and the control power source unit 2 being thus operated, during fluorescence photographing, when the external power source apparatus 1 is connected, the external power source apparatus 1 is actuated, whereby a photographing mode conforming to the intended purpose is assumed.

Figure 4:
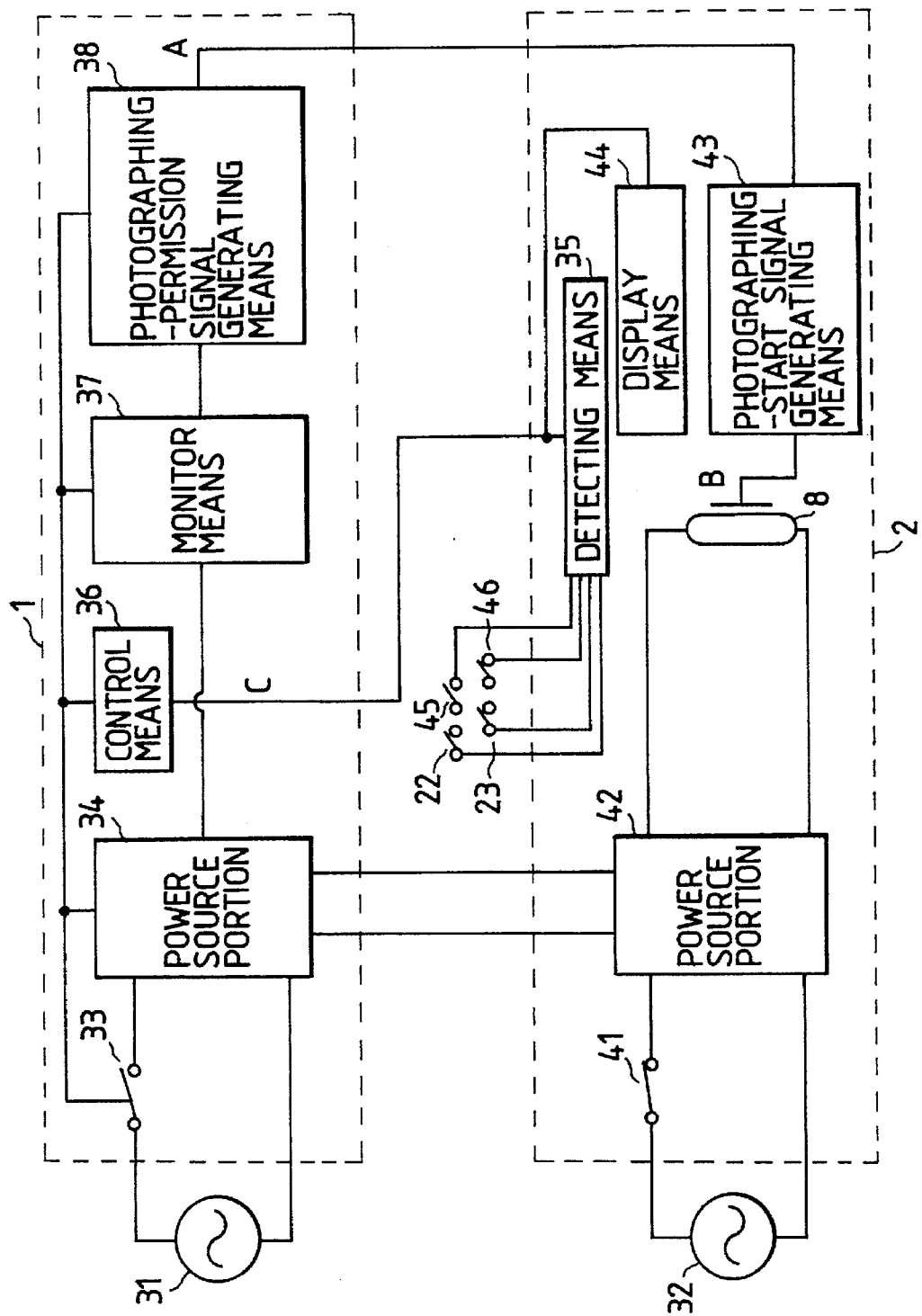
FIG. 4 is a block circuit diagram of a power source portion.

FIG. 4 shows a modification of the power source portion, in which the detecting means 35 for detecting the deficiency of the amount of light needed for photographing provided in the external power source apparatus 1 is provided in the control power source unit 2. Again by this, a similar operational effect is obtained.

Figure 5:
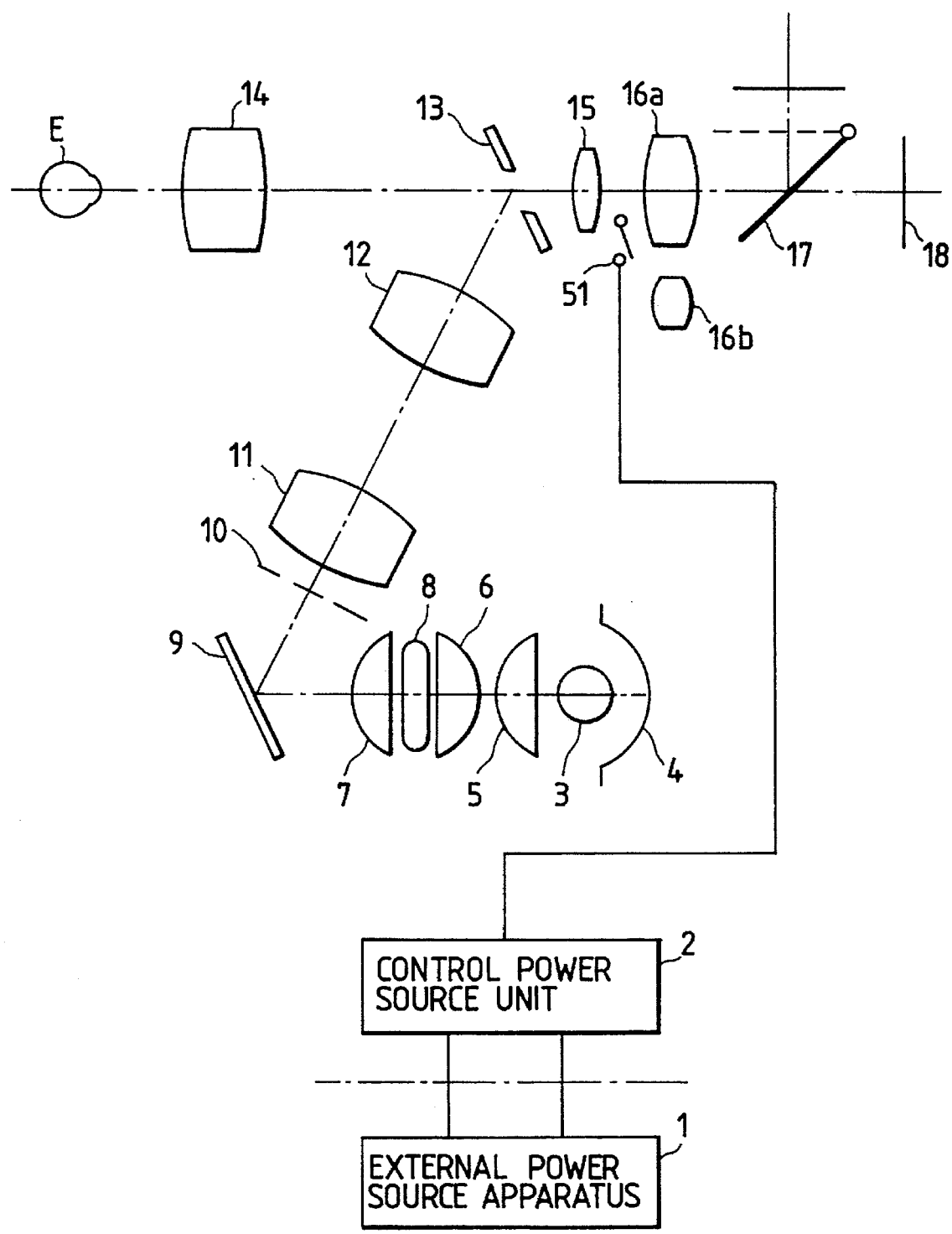
FIG. 5 shows the construction of a second embodiment of the present invention.

FIG. 5 shows a second embodiment of the present invention which is designed to use the external power source apparatus 1 when the imaging lenses 16a and 16b are interchanged, whereby a light amount for photographing becomes necessary. A provision is made of a detection switch 51 adapted to be closed only when of the imaging lenses 16a and 16b for changing over the photographing magnification, the imaging lens 16b used for enlarged photographing, is inserted into the optical path. A detection signal S3 from the detection switch 51 is inputted to the control power source unit 2 as in the case of the first embodiment.

Figure 6:
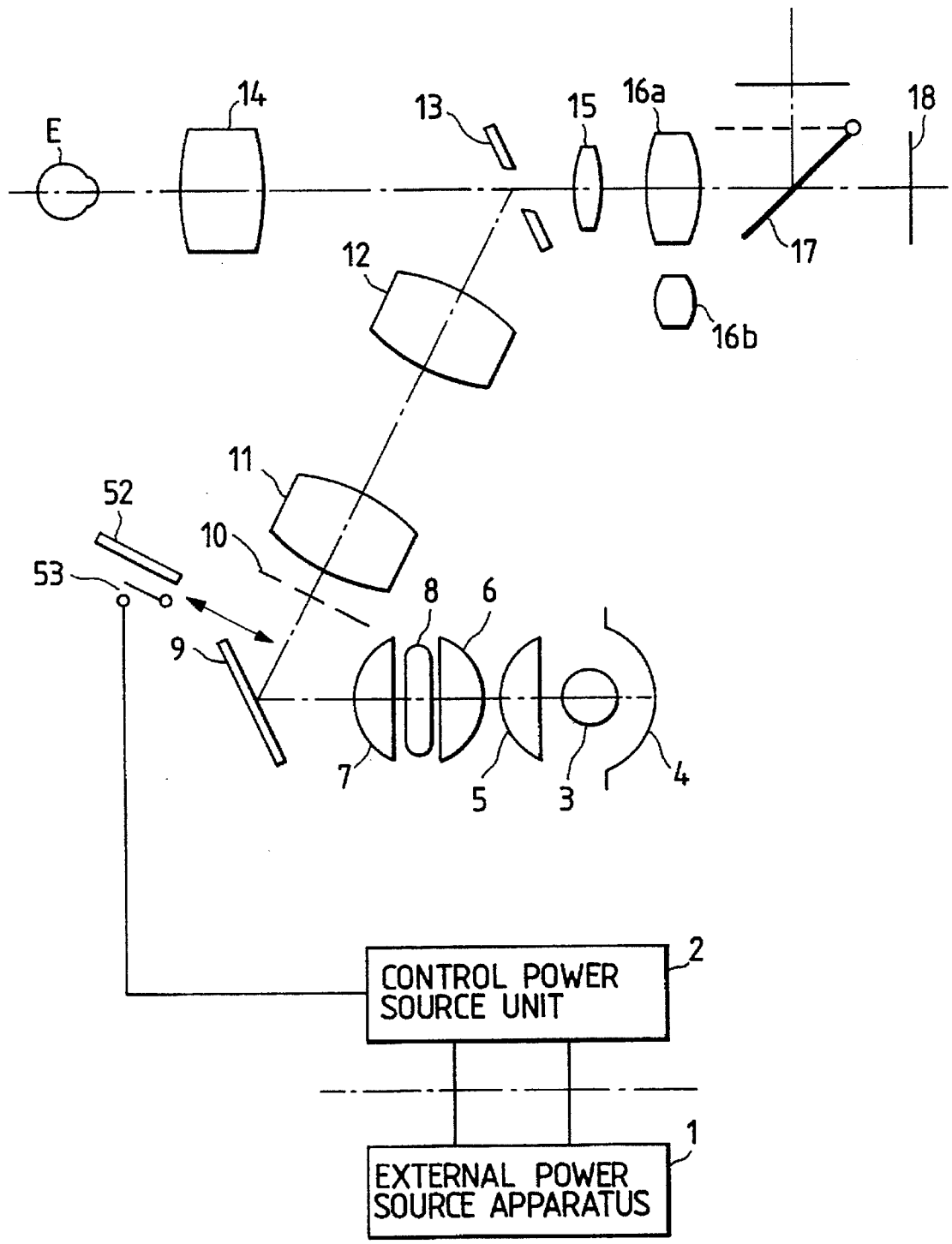
FIG. 6 shows the construction of a third embodiment of the present invention.

FIG. 6 shows a third embodiment of the present invention which is designed to use the external power source apparatus 1 when a filter other than the fluorescence filter is inserted into the optical path whereby an amount of light for photographing becomes necessary. A provision is made to provide a detection switch 53 adapted to be closed only when a filter 52 other than the filter for fluorescence photographing is inserted. A detection signal S4 from the detection switch 53 is inputted to the control power source unit 2 as in the first embodiment.

Further, when as in the first embodiment, it is determined by the switch 45 for shortening the photographing interval and the switch 46 for setting the light amount for photographing that the light amount is deficient by the pre-inputted supply energy of the power source portion 42 of the control power source unit 2, an external power source actuating signal C is outputted from the detecting means 35 to operate the external power source apparatus 1 and the control power source unit 2, whereby when the external power source apparatus 1 is connected during enlarged photographing, the external power source apparatus 1 is actuated, and a photographing mode conforming to the intended purpose is assumed.

Figure 7:
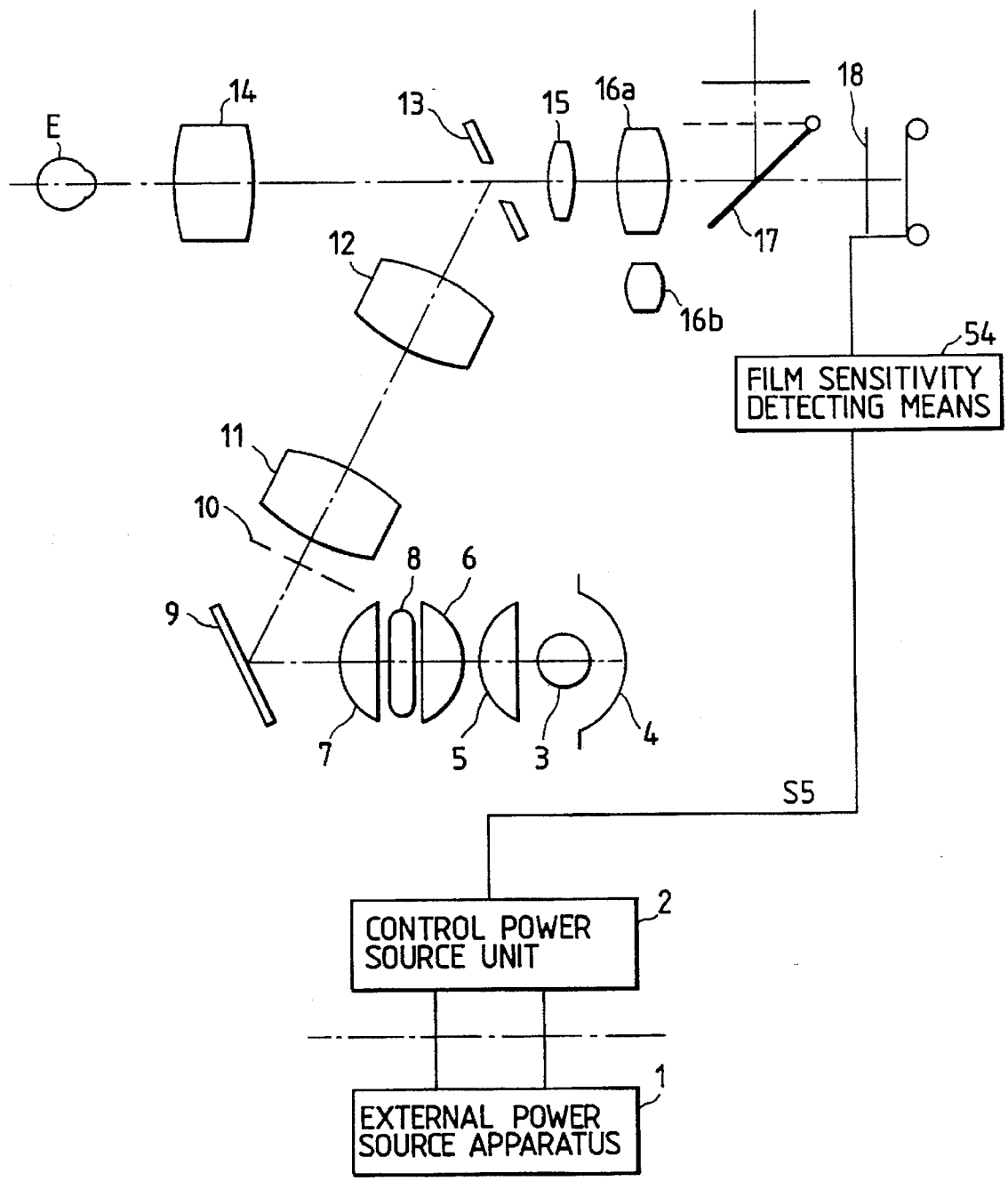
FIG. 7 shows the construction of a fourth embodiment of the present invention.

FIG. 7 shows a fourth embodiment of the present invention which is designed to use the external power source apparatus 1 when photographing film of low sensitivity is used, whereby a light amount for photographing becomes necessary. Film sensitivity detecting means 54 is provided near the film 18, and this film sensitivity detecting means 54 outputs a detection signal S5 when the film 18 of low sensitivity is inserted. The detection signal S5 from the film sensitivity detecting means 54 is inputted to the control power source unit 2 as in the first embodiment.

Further, when as in the first embodiment, it is determined by the switch 45 for shortening the photographing interval and the switch 46 for setting the light amount for photographing that the light amount for photographing is deficient by the pre-inputted supply energy of the power source portion 42 of the control power source unit 2, the external power source actuating signal C is outputted from the detecting means 35 to operate the external power source apparatus 1 and the control power source unit 2, whereby when the external power source apparatus 1 is connected during the photographing by the film 18 of low sensitivity, the external power source apparatus 1 is actuated, and a photographing mode conforming to the intended purpose is assumed.

Figure 8:
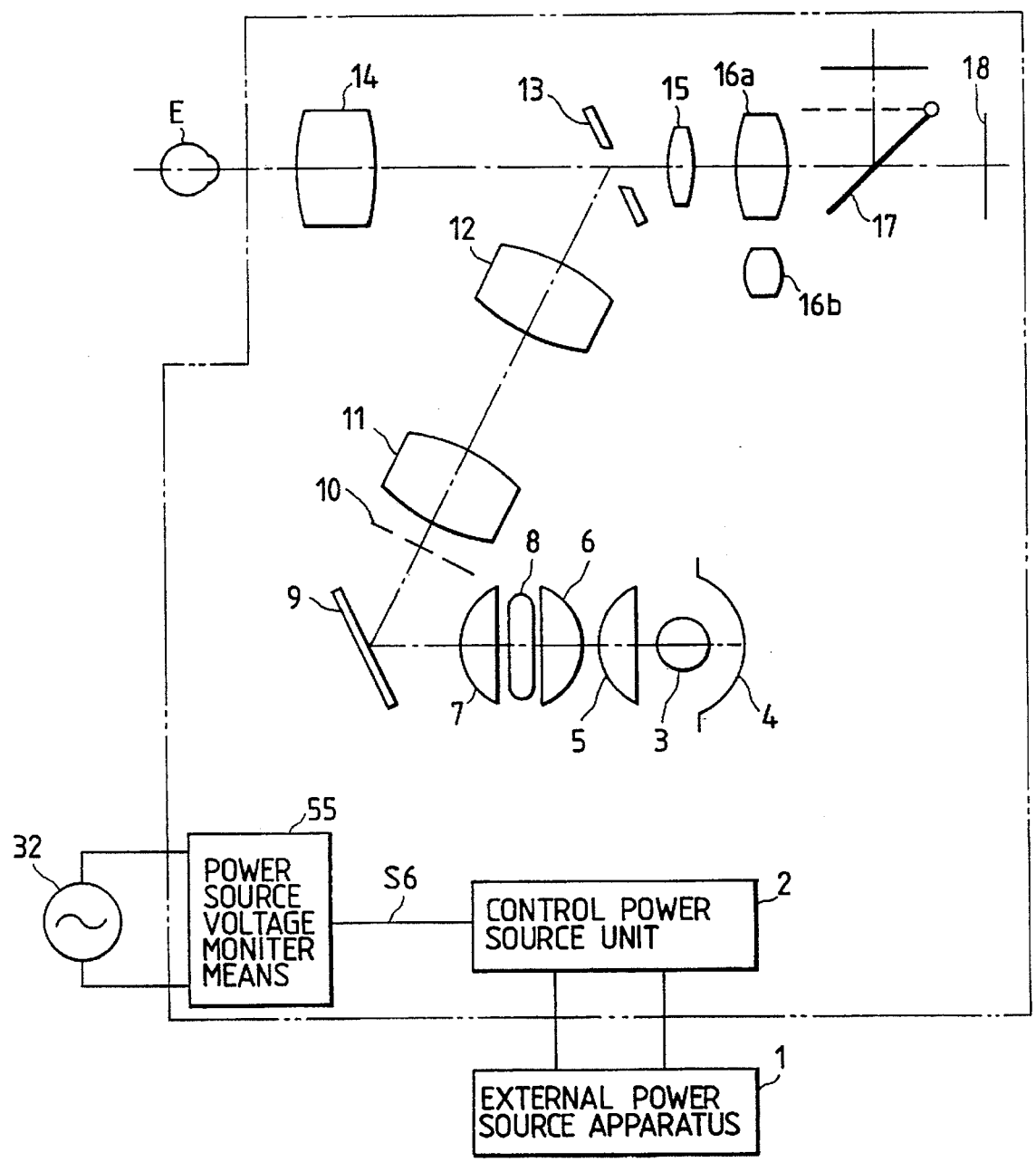
FIG. 8 shows the construction of a fifth embodiment of the present invention.

FIG. 8 shows a fifth embodiment of the present invention which is designed to use the external power source apparatus 1 when the voltage of the commercially available power source 32 drops and the light amount for photographing becomes deficient by the power source of the control power source unit 2, whereby a light amount for photographing becomes necessary. Power source voltage monitor means 55 is provided in the control power source unit 2, and a detection signal S6 is outputted when the voltage of the commercially available power source 32 drops. The detection signal S6 from the power source voltage monitor means 55 is inputted to the control power source unit 2 as in the first embodiment.

Further, when as in the first embodiment, it is determined by the switch 45 for shortening the photographing interval and the switch 46 for setting the light amount for photographing that the light amount for photographing is deficient by the pre-inputted supply energy of the power source portion 42 of the control power source unit 2, the external power source actuating signal C is outputted from the detecting means 35 to operate the external power source apparatus 1 and the control power source unit 2, whereby when the external power source apparatus 1 is connected when the source voltage of the commercially available power source 32 has dropped, the external power source apparatus 1 is actuated, and a photographing mode conforming to the intended purpose is assumed.

The commercially available power source 31 supplied to the external power source apparatus 1 can also be supplied via the control power source unit 2.

Figure 9:
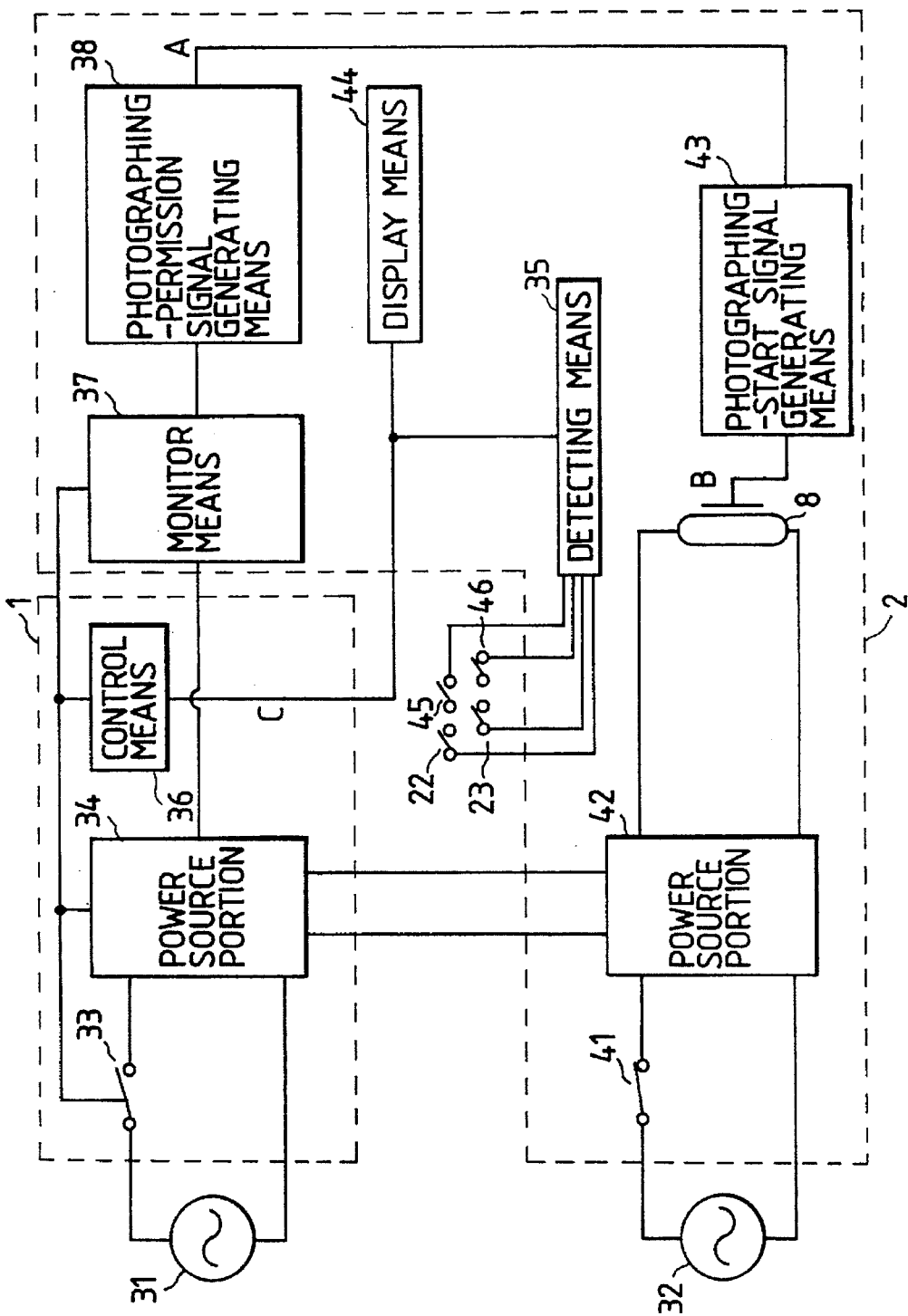
FIG. 9 is a block circuit diagram of a power source portion.

FIG. 9 shows another modification of the power source portion, in which the monitor means 37 for monitoring the voltage of the power source portion 34 of the external power source apparatus 1 and the photographing permission signal generating means 38 are provided in the control power source unit 2.

Figure 10:
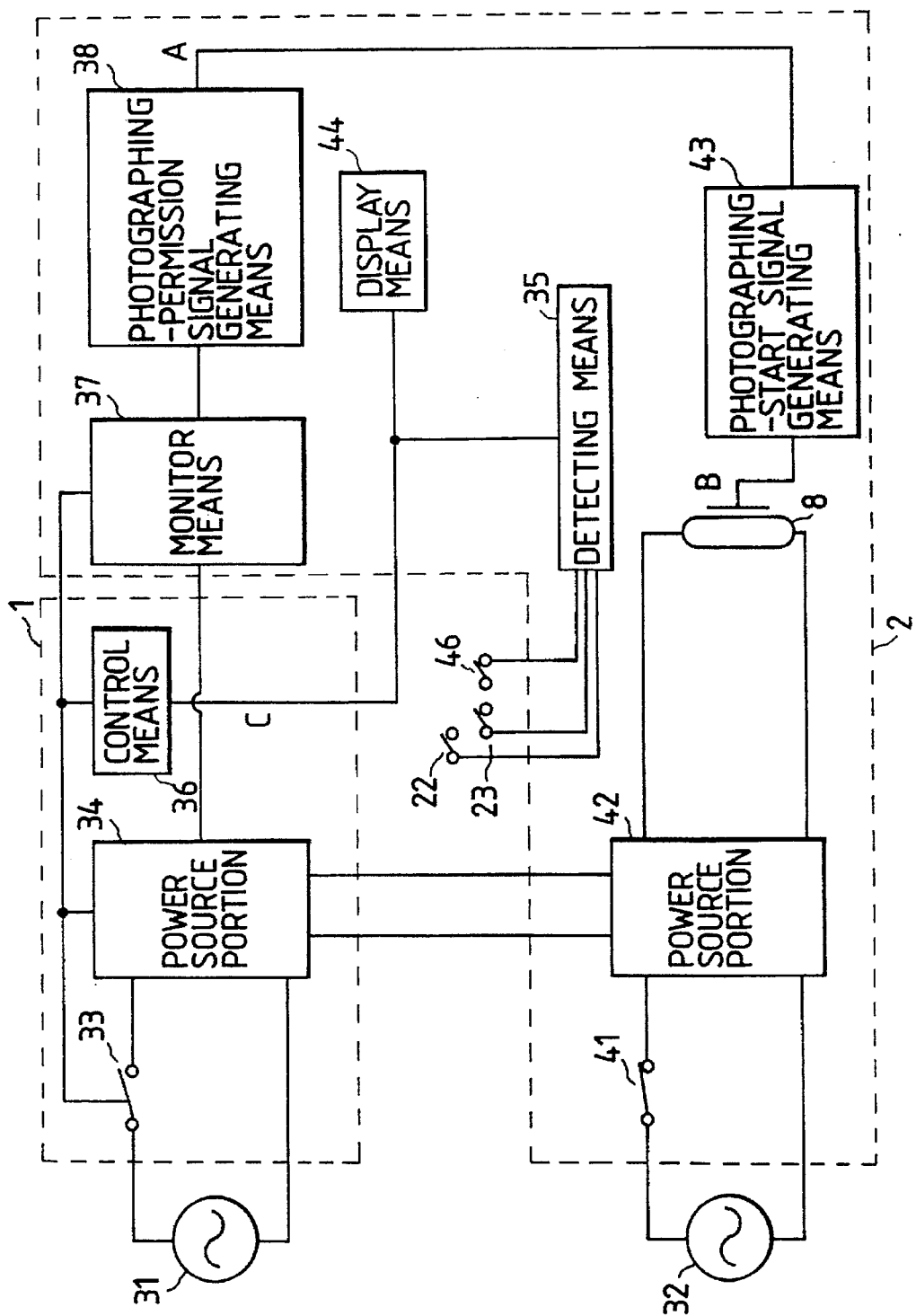
FIG. 10 is a block circuit diagram of a power source portion.

FIG. 10 shows a modification of the power source portion shown in FIG. 9. In this modification, the switch 45 for shortening the photographing interval is eliminated and design is made such that the photographing interval is shortened by the power source switch 33 of the external power source apparatus 1.

The external power source apparatus 1 can be applied not only during fluorescence photographing, but also during ordinary ophthalmological photographing.

What is claimed is:

1. An ophthalmological imaging apparatus comprising:
   a main body portion for effecting the imaging of an eye to be examined, said main body portion having a light source producing light for the imaging of the eye to be examined;
   power source means provided in said main body portion, said power source means supplying electrical energy for the production of light to said light source; and
   connecting means, provided in said main body portion, for connecting thereto an external power source apparatus for supplying from the outside of said main body portion electrical energy to said light source corresponding to the deficiency in the amount of light from said light source produced by the electrical energy from said power source means relative to a desired amount of light for imaging.

2. The apparatus according to claim 1, further comprising means for detecting that the produced amount of light from said light source produced in response to the electrical energy from said power source means is deficient relative to the desired light amount for imaging.

3. The apparatus according to claim 1, wherein the electrical energy from said external power source apparatus connected to said connecting means is used during fluorescence imaging.

4. The apparatus according to claim 1, wherein the electrical energy from said external power source apparatus connected to said connecting means is used during enlarged imaging.

5. The apparatus according to claim 1, wherein the electrical energy from said external power source apparatus connected to said connecting means is used when a filter is used for the imaging of the eye to be examined by said main body portion.

6. The apparatus according to claim 1, wherein the electrical energy from said external power source apparatus connected to said connecting means is used during the use of low sensitivity film.

7. The apparatus according to claim 1, wherein the electrical energy from said external power source apparatus connected to said connecting means is used when the voltage of said power source means drops.

8. An ophthalmological imaging apparatus comprising:
   a main body portion for effecting imaging of an eye to be examined, said main body portion having a light source producing light for the imaging of the eye to be examined;
   power source means provided in said main body portion, said power source means supplying electrical energy for the production of light to said light source; and
   external power source means provided discretely from said main body portion, said external power source means supplying from the outside of said main body portion electrical energy to said light source corresponding to the deficiency in the amount of light from said light source produced by the electrical energy from said power source means relative to a desired amount of light for imaging.

9. The apparatus according to claim 8, further comprising means for detecting that the produced amount of light from said light source produced in response to the electrical energy from said power source means is deficient relative to the desired light amount for imaging.

10. The apparatus according to claim 8, wherein the electrical energy from said external power source means is used during fluorescence imaging.

11. The apparatus according to claim 8, wherein the electrical energy from said external power source means is used during enlarged imaging.

12. The apparatus according to claim 8, wherein the electrical energy from said external power source means is used when a filter is used for the imaging of the eye to be examined by said main body portion.

13. The apparatus according to claim 8, wherein the electrical energy from said external power source means is used during the use of low sensitivity film.

14. The apparatus according to claim 8, wherein the electrical energy from said external power source means is used when the voltage of said power source means drops.

15. An external power source apparatus for use with an ophthalmological imaging apparatus including a light source producing light for the imaging of an eye to be examined, and power source means for supplying electrical energy for the production of light to said light source, said external power source being connected to the ophthalmological imaging apparatus for executing the imaging of the eye to be examined, said external power source apparatus comprising:

a connecting portion for connection to the ophthalmological imaging apparatus; and external power source means for storing electrical energy corresponding to the deficiency in the amount of light for said light source produced by the electrical energy from said power source means relative to a desired light amount for imaging and for supplying to said light source of the ophthalmological imaging apparatus the stored electrical energy through said connecting portion so that the stored electrical energy is supplied to said light source with the energy from said power source means.

\* \* \* \* \*

UNITED STATES PATENT AND TRADEMARK OFFICE
CERTIFICATE OF CORRECTION

PATENT NO. : 5,630,179
DATED : May 13, 1997
INVENTOR(S) : Nobuyoshi KISHIDA

It is certified that error appears in the above-identified patent and that said Letters Patent is hereby corrected as shown below:

COVER PAGE, [56], line 6, delete "Yammamoto" and insert therefor --Yamamoto--.

Column 3, line 52, after "photographing", insert --is set--; and
    Line 52, delete "judged" and insert therefor --determined--.

Column 4, line 47, delete "of" and insert therefor --to provide--; and
    Line 48, after "when", insert a comma (",").

Signed and Sealed this

Ninth Day of December, 1997

Attest:

BRUCE LEHMAN

Attesting Officer    Commissioner of Patents and Trademarks